United States Patent [19]
Baker et al.

[11] Patent Number: 5,339,818
[45] Date of Patent: Aug. 23, 1994

[54] METHOD FOR DETERMINING BLOOD PRESSURE UTILIZING A NEURAL NETWORK

[75] Inventors: Phillip D. Baker; Joseph A. Orr; Dwayne R. Westenskow; Timothy P. Egbert, all of Salt Lake City, Utah

[73] Assignee: University of Utah Research Foundation, Salt Lake City, Utah

[21] Appl. No.: 119,451

[22] Filed: Sep. 9, 1993

Related U.S. Application Data

[63] Continuation of Ser. No. 961,031, Oct. 14, 1992, abandoned, which is a continuation of Ser. No. 575,947, Aug. 31, 1990, abandoned, which is a continuation-in-part of Ser. No. 410,115, Sep. 20, 1989, abandoned.

[51] Int. Cl.$^5$ .............................................. A61B 5/00
[52] U.S. Cl. ................................... 128/677; 128/680; 364/413.03; 395/924
[58] Field of Search .................................. 395/22, 924; 128/677–685; 364/413.03

[56] References Cited

U.S. PATENT DOCUMENTS

| | | |
|---|---|---|
| 3,568,075 | 3/1971 | Dusbeck . |
| 4,263,918 | 4/1981 | Swearingen et al. . |
| 4,326,259 | 4/1982 | Cooper et al. . |
| 4,461,301 | 7/1984 | Ochs . |
| 4,463,764 | 8/1984 | Anderson et al. . |
| 4,519,395 | 5/1985 | Hrushesky . |
| 4,658,358 | 4/1987 | Leach et al. . |
| 4,688,577 | 8/1987 | Bro . |

(List continued on next page.)

OTHER PUBLICATIONS

"Natural Underwater Sounds Identification by Use of Neural Networks and Linear Techniques," Legitimus et al. Jul. 1990.

"An Introduction to Computing with Neural Nets", Lippman, Richard P. *IEEE ASSP MAGAZINE*, (Apr. 1978) pp. 4 through 22.

"Neural Computers" Stubs, Derek F. *M. D. Computing.* vol. 5: (3) pp. 1–12, 1988.

"Use of Neural Networks for Detection of Artifiacts in Arterial Pressure Waveforms", Anthony V. Sebald PH.D.

"Heart Sound Analysis Using Neural and Statistical Classifiers; A Comparison", Barschdorff, Dieter, Bothe, Achim, Rengshausen, Ute.

"Training Neural Networks for ECG Feature Recognition" K. Zhu, P. D. Noakes and A. D. P. Green.

"New Methods for ECG Classification-A Comparative Study" D. Edelstein, M. Fleslsher, G. F. Inbar.

*Primary Examiner*—Lee S. Cohen
*Assistant Examiner*—Robert L. Nasser
*Attorney, Agent, or Firm*—Thorpe, North & Western

[57] ABSTRACT

A method and device for indirect, quantitative estimation of blood pressure attributes and similar variable physiological parameters utilizing indirect techniques. The method of practice includes (i) generating a sequence of signals which are quantitative dependent upon the variable parameter, (ii) transmitting and processing the signals within a computer system and associated neural network capable of generating a single output signal for the combined input signals, (iii) directly determining an actual value for the parameter concurrent with the indirect generation of signals of the previous steps, (iv) applying weighting factors within the neural network at interconnecting nodes to force the output signal of the neural network to match the true value of the parameter as determined invasively, (v) recording the input signals, weighting factors and true value as training data within memory of the computer, and (vi) repeating the previous steps to develop sufficient training data to enable the neural network to accurately estimate parameter value upon future receipt of on-line input signals. Procedures are also described for preclassification of signals and artifact rejection. Following training of the neural network, further direct measurement is unnecessary and the system is ready for diagnostic application and noninvasive estimation of parameter values.

13 Claims, 10 Drawing Sheets

U.S. PATENT DOCUMENTS

| | | |
|---|---|---|
| 4,694,418 | 9/1987 | Ueno et al. . |
| 4,718,427 | 1/1988 | Russell . |
| 4,719,591 | 1/1988 | Hopfield et al. . |
| 4,750,153 | 6/1988 | Owechko et al. . |
| 4,760,437 | 7/1988 | Denker et al. . |
| 4,774,960 | 10/1988 | Arnold et al. . |
| 4,781,200 | 11/1988 | Baker . |
| 4,792,915 | 12/1988 | Adams et al. . |
| 4,796,199 | 1/1989 | Hammerstrom et al. . |
| 4,796,639 | 1/1989 | Snow et al. . |
| 4,803,736 | 2/1989 | Grossberg et al. . |
| 4,805,225 | 2/1989 | Clark . |
| 4,830,019 | 5/1989 | Shirasaki et al. . |
| 4,838,275 | 6/1989 | Lee . |
| 4,854,324 | 8/1989 | Hirschman et al. . |
| 4,869,266 | 9/1989 | Taylor et al. . |
| 4,974,597 | 12/1990 | Walloch ................ 128/680 |
| 5,014,714 | 5/1991 | Millay et al. ......... 128/680 |
| 5,022,403 | 6/1991 | LaViola ................ 128/680 |
| 5,060,279 | 10/1991 | Crawford ............... 382/14 |
| 5,092,343 | 3/1992 | Spitzer et al. . |

$$y = f\left(\sum_{i=0}^{m} x_i \, w_i - \theta\right)$$

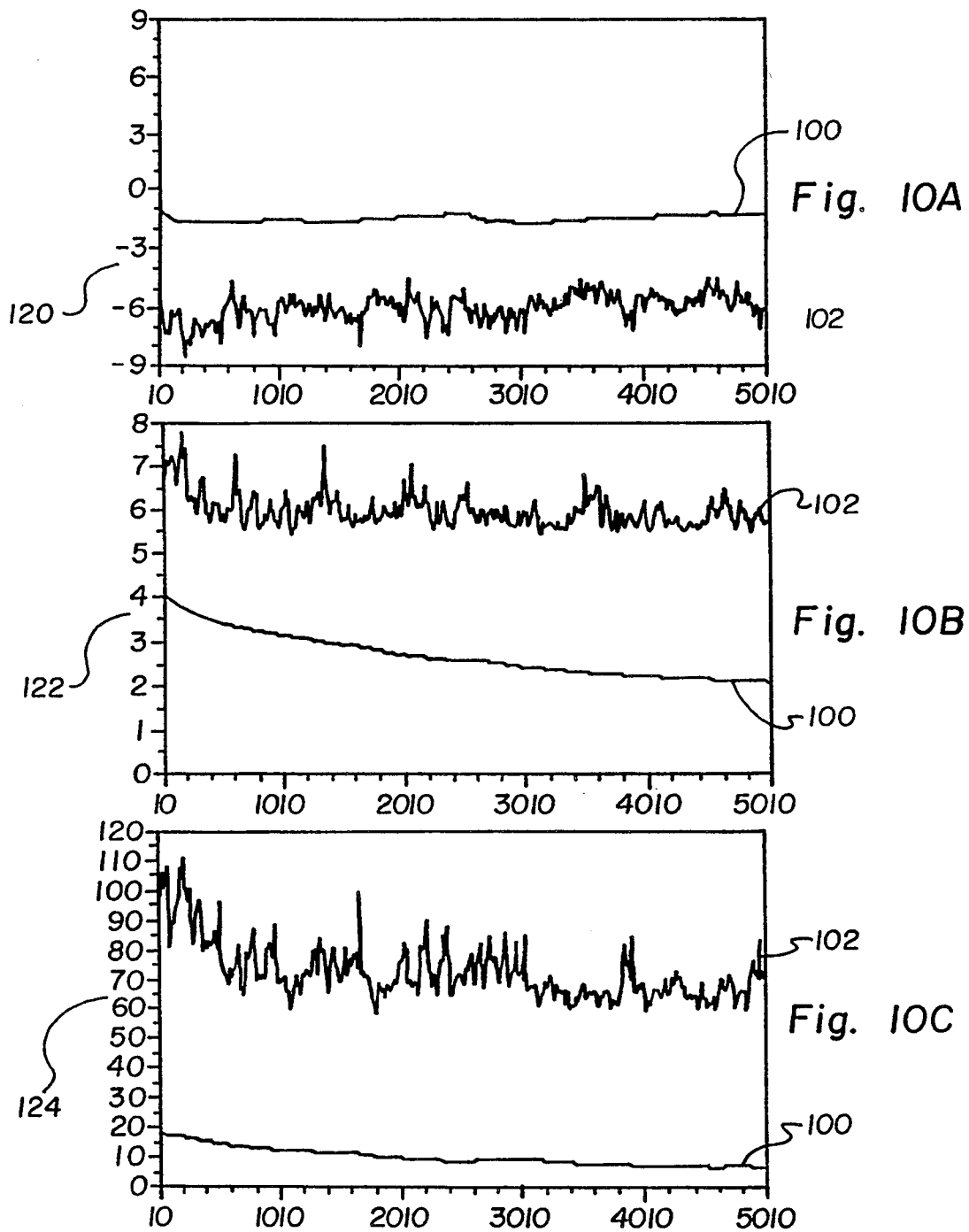

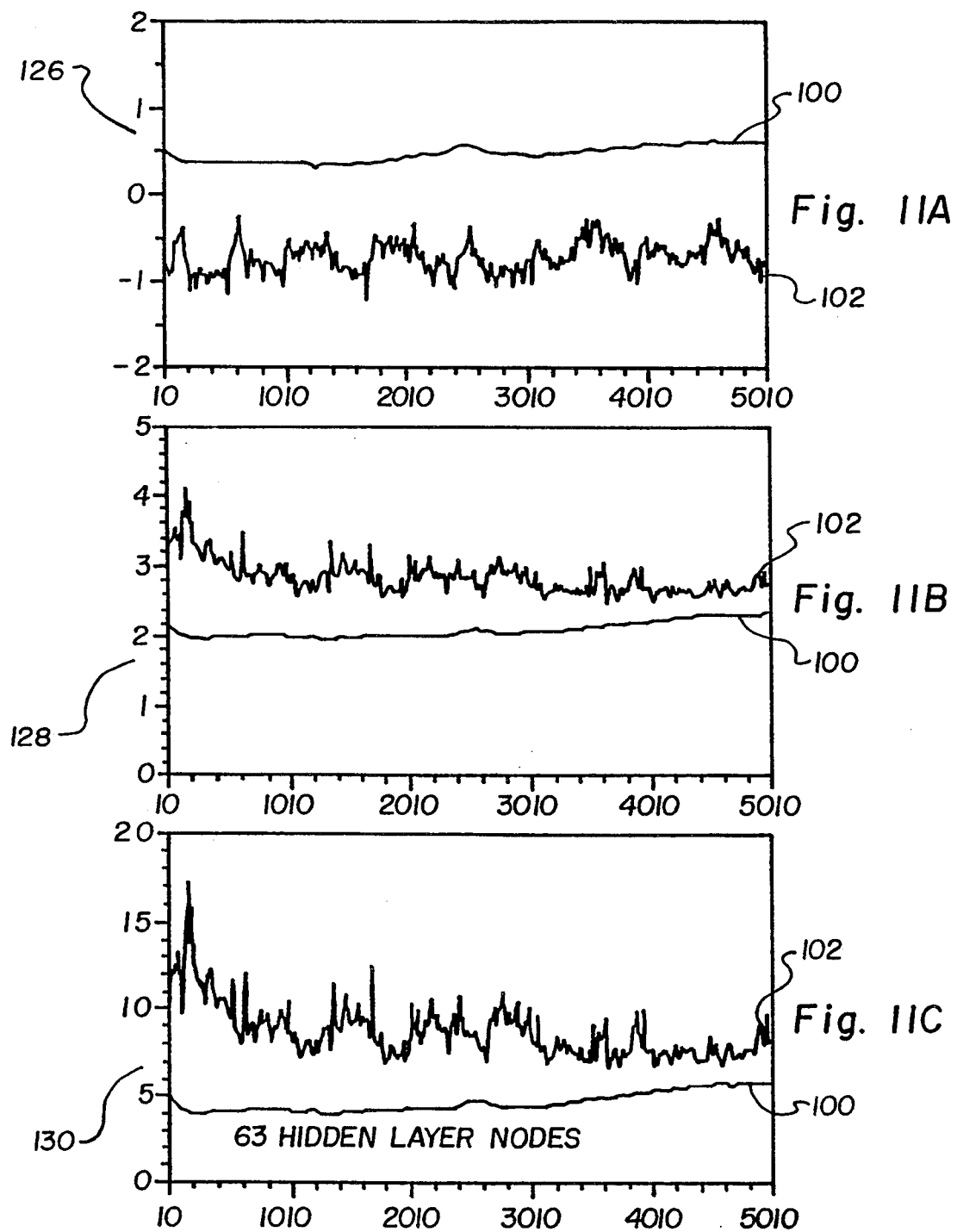

METHOD FOR DETERMINING BLOOD PRESSURE UTILIZING A NEURAL NETWORK

This application is a continuation of U.S. Ser. No. 07/961031, filed Oct. 14, 1992, now abandoned, which is a continuation of U.S. Ser. No. 07/575947, filed Aug. 31, 1990, now abandoned, which is a continuation in part of a previously filed patent application entitled DEVICE AND METHOD FOR NEURAL NETWORK BREATHING ALARM, filed on Sep. 20, 1989 under Ser. No. 07/410,115 now abandoned.

BACKGROUND OF THE INVENTION

1. Field of the Invention

Present invention relates to a device and method for calculation of variable physiological parameters such as blood pressure utilizing a neural network. More particularly, the present invention relates to a method for training a neural network to recognize and calculate blood pressure values based on an oscillometric waveform generated by an external blood pressure cuff.

2. Prior Art

Blood pressure is one of the primary physiological measurements used to access the condition of a patient's cardiovascular system. During acute care, as is provided in the operating room and intensive care unit, blood pressure measurements are routinely used to monitor and manage the condition of patients.

Because noninvasive methods of estimating blood pressure are generally a traumatic and present little risk to the patient, they are often used instead of the invasive method, which requires that a catheter or needle be inserted into an artery. A major disadvantage associated with noninvasive methods has been their lack of close agreement with actual blood pressure as would be measured by an invasive method. In addition, lack of close agreement also exists between different noninvasive methods, further adding to the uncertainty of any particular reading derived by noninvasive methods.

Oscillometry has become the most common method used for automatic, noninvasive blood pressure monitoring. One advantage of the oscillometric method over other noninvasive methods is its ability to estimate not only diastolic and systolic pressures, but also mean pressure. Conventional oscillometric blood pressure monitors use an inflatable air filled occlusive cuff that is placed around a limb, usually the upper arm. Small oscillations in the cuff pressure, which correspond to intraarterial pulses in the artery underlying the cuff, are recorded while the cuff pressure is increased from a pressure below diastolic to a cuff pressure, reach a maximum amplitude at cuff pressure, between diastolic and systolic pressure, and then decrease in amplitude with further increases in cuff pressure above systolic. As is characteristic of oscillometric waveforms, the cuff pressure oscillations initially increase in amplitude with increasing cuff pressure.

Although oscillometry has become the most prominent noninvasive blood pressure monitoring method, there is still a general lack of theoretical understanding regarding the origin of the oscillometric waveform and the relationship between that waveform and the respective attributes of blood pressure identified as diastolic, mean and systolic pressure. This lack of theoretical understanding has led to the development of empirical algorithms which serve to estimate diastolic, mean, and systolic blood pressure.

For example, it is generally believed that the minimum cuff pressure at which the cuff pressure oscillations reach their maximum provides a reasonable estimate of mean blood pressure. The maximum amplitude criteria, however, apparently underestimates true mean blood pressure and is dependent for accuracy on such factors as the magnitude of the intraarterial pulse pressure. The maximum amplitude criteria does not therefore provide ideal measurements in all conditions.

Fixed ratio amplitude criteria have been used in commercial blood pressure monitors to estimate systolic and diastolic pressures. Such fixed ratio amplitude criteria involve identifying the cuff pressure at which the oscillations have decreased from the maximum by a fixed amount, such as fifty or eighty percent. Here again, fixed ratio amplitude criteria are dependent for accuracy on such factors as the magnitude of the intraarterial pulse pressure. The accuracy of such fixed ratio methods is dependent on empirical observations and has yet to be explained in theory.

In short, blood pressure monitoring as represented by amplitude oscillometry processed by conventional algorithms merely generalizes relationships which are based on minimum cuff pressure versus maximum oscillation for mean blood pressure and some empirical percentage under the fixed ratio amplitude criteria for estimating systolic and diastolic pressures. Comparison of conventional noninvasive measurement techniques with invasive measurements of blood pressure has shown that noninvasive estimates may vary as much as forty percent from true value.

At least three factors play a dominant role in limiting the performance of conventional oscillometric algorithms. First, oscillometric waveforms are susceptible to artifacts and noise from a variety of sources. Typical algorithms are not capable of dealing with artifacts, common noise and other variations which may be reflected in the oscillometric waveform. In fact, most conventional oscillometric algorithms are based either directly or indirectly on the assumption that blood pressure remains constant during the recording period, which may last as much as ten to thirty seconds. It is apparent that the processing of artifacts and noise interferring with quality signals degenerates the accuracy of any estimation of blood pressure. When this is combined with the occurrence of cyclic changes in blood pressure during recording of the oscillometric waveform, it becomes clear that the accuracy and usefulness of oscillometric estimates are at best an indicator of probable blood pressure rather than an accurate determination.

A second factor that limits the performance of conventional oscillometric algorithms is the over simplistic practice of empirically interpreting the relationship between the oscillometric waveform and arterial blood pressure attributes to be a uniform percentage. This is an over simplification because this relationship in fact varies with changes in arterial blood pressure and pulse pressure. To generalize that values for diastolic pressures are best estimated by identifying the cuff pressure at which the oscillations have decreased by eighty percent from the maximum is at best a general guide. Although there have been a number of attempts to develop more sophisticated algorithms which deal with pulse transformations through pressure-volume curves, these algorithms depend on identification of subtle features within the oscillometric waveform which are very sensitive to artifacts and noise and are difficult to implement in a robust and practical form.

A third factor that limits the performance of conventional oscillometric algorithms is the nonlinear relationship between the oscillometric waveform and intraarterial blood pressure. The relationship is further complicated by also being non-stationary with respect to time and subjects. For example, the shape of the oscillometric waveform is strongly dependent on the state of the cardiovascular system and the interaction of intraarterial pressure pulses with the nonlinear mechanical properties of the arteries. The fact that these relationships change with activity, age and disease further complicates use of an algorithm which tends to generalize relationships between the oscillometric waveform and blood pressure attributes.

Most common pressure monitoring systems include blood pressure estimations based on the shape of the oscillometric pulses rather than the amplitude. This approach has likewise been subject to the problems set forth in the preceding paragraphs. Specifically, such methods require high fidelity recording of the oscillometric signal and tend to be very sensitive to signal noise and artifacts.

What is needed therefore is a fresh approach to the evaluation of the oscillometric signals and waveform for blood pressure measurement which overcomes the (i) regular occurrence of noise and artifacts which regularly occur during blood pressure monitoring, (ii) nonlinear relationship and (iii) lack of theoretical understanding.

OBJECTS AND SUMMARY OF THE INVENTION

It is an object of the present invention to provide a method and device for collecting and processing noninvasive oscillometric blood pressure data and processing such data for a more accurate estimation of intraarterial diastolic, mean and systolic blood pressures.

It is a further object of the present invention to provide a device and method for estimating a variable physiological parameter such as blood pressure without the need for making a direct, invasive measurement, while providing accuracy which more closely approaches the direct measurement.

It is a further object of the present invention to provide a device and method for estimating physiological parameters such as blood pressure utilizing a neural network as a system for processing input data and ultimately computing the values of physiological parameters.

It is yet another object of the present invention to provide a device and method for generating a body of training data for use as part of a neural network to assist in estimation and determination of physiological parameter values derived from generated data having a nonlinear relationship with the parameter values.

A still further object of the present invention is to provide a method and device for determining the values of physiological parameters despite occurrence of artifacts, noise and other corrupting signal influences.

Another object of the present invention is to provide a device and method for determining blood pressure and other similar physiological parameters without a need for reliance upon generalizing assumptions which undermine system accuracy.

These and other objects are realized in a method for indirect, quantitative estimation of a variable physiological parameter based on indirect as opposed to direct measurement of parameter value. The method comprises the steps of (i) identifying the physiological parameter to be quantitatively monitored and estimated; (ii) generating a sequence of signals which are quantitatively dependent upon the variable physiological parameter, but which are not suitable for providing a direct quantitative readout based on direct measurement of the parameter; (iii) transmitting the signals to and processing such signals within a computer system including input nodes of a neural network supported by the computer system, which neural network is capable of generating at least one output signal for the combined input signals as an accurate estimate of the estimated value for the physiological parameter; (iv) determining an actual, true value for the physiological parameter concurrent with the previous steps; (v) making within the neural network which modify the value of the output signal to match the true value of the physiological parameter determined in the previous step; recording as training data within memory of the computer system the input signals, and true values associated with the sequence of signals generated under step ii; and sequentially repeating the previous steps sufficient to train the neural network to recognize relevant input signals and estimate the value of the physiological parameter based on association of on-line input signals with one or more trained neural networks. A device is also disclosed for implementing the above inventive method, as well as specific adaptations with respect to systolic, mean and diastolic blood pressure. Also disclosed is a neural network for pre-classifying waveforms and for disregarding noise and artifact signals.

Other objects and features of the present invention will be apparent to those skilled in the art based on the following detailed description, taking in combination with the accompanying drawings.

DESCRIPTION OF DRAWINGS

FIGS. 10a, 10b and 10c provide graphic representations of neural network learning curves generated with respect to testing.

FIGS. 11a, 11b and 11c provide graphic representation of performance curves as generated with respect to the test animals.

DESCRIPTION OF PREFERRED EMBODIMENT

Figure 1:
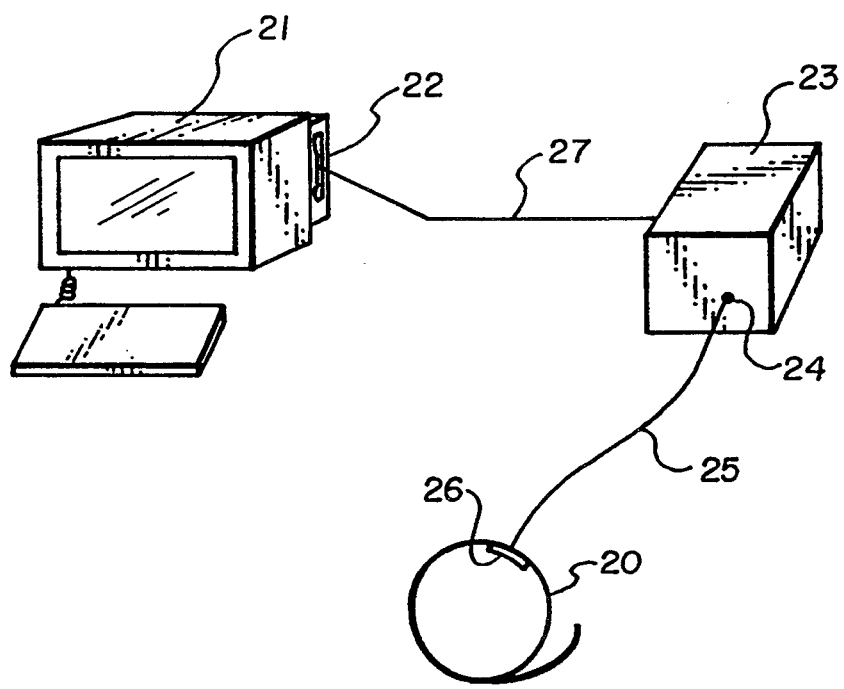
FIG. 1 is a graphic representation of components making up a conventional oscillometric blood pressure monitoring system.

FIG. 1 illustrates a block diagram of a blood pressure monitor and processing system constructed in accordance with principles of the present invention. This includes a blood pressure cuff 20 which is adapted with suitable hardware necessary to pressurize the cuff in accordance with conventional practice. This cuff 20 may be a banded configuration typically applied to limbs or extremities of a patient or may be a superficial temporal artery blood pressure monitor as applied to the patients head. For purposes of the disclosure set forth initially herein, a temporal artery blood pressure pad is disclosed. However, it would be apparent to those skilled in the art that a conventional occlusive blood pressure cuff could likewise be substituted in application of the present inventive principles.

The cuff 20 interfaces at a pulse side of the patient to generate noninvasive, oscillometric blood pressure data which is processed in a computer 21. The computer is connected through a parallel interface card 22 to a satellite box 23 which contains the hardware necessary to inflate and measure the pressure in a transducer bladder of the cuff 20.

A software controlled direct current Romega 80 air pump is used to inflate the transducer bladder. Although most oscillometric blood pressure oscillometric monitors employ a deflation ramp, a software controlled direct current Romega 80 air pump is used to inflate the transducer bladder. Although most oscillometric blood pressure monitors employ a deflation ramp to record the oscillometric waveform, the superficial temporal artery monitor employs an inflation ramp. To damp out pump oscillations and provide a smooth pressure ramp for inflating the transducer bladder, the output of the air pump is fed through two rigid volume chambers of 10 ml each, separated by a pneumatic resistance. A manually adjustable needle valve 24 is used to control the flow rate from the damping chambers to the transducer bladder, thus allowing for variable pressure ramp rates. The transducer bladder of the superficial temporal artery blood pressure pad is connected to the output of the needle valve 24 through an air line 25 approximately 1.5 meters long with an inside diameter of approximately 1.5 millimeters. A secondary line is connected from the output of the needle valve 24 to a pressure transducer and a software controlled solenoid valve. The pressure transducer is used to record the inflation ramp and oscillometric waveform from the superficial temporal artery blood pressure pad transducer bladder. The solenoid valve serves as a dump valve to release the pressure in the transducer bladder following each blood pressure determination. With respect to FIG. 1, it will be apparent to those skilled in the art that the satellite box 23 houses the pump and pneumatic circuit, pressure transducer, analog amplifier/filter, 12 bit analog-to-digital converter and parallel port. This combined hardware services the inflation needs of the cuff 20, and provides initial filtering and processing of signals. Digital signals are then transmitted over connecting line 27 to the computer interface card 22. Software within the computer 21 controls subsequent data collection, processing and data display.

The oscillometric waveform comprises transducer bladder pressure oscillations plotted as a function of transducer bladder pressure and is constructed by software using the derivative of the transducer bladder pressure signal. The derivative of the transducer bladder pressure is the sum of the changes in pressure due to the inflation ramp and of the changes in pressure due to volume oscillations transmitted from the underlying artery. The goal in reconstructing the oscillometric waveform is to isolate the component of the derivative signal corresponding to the volume oscillations from the derivative signal and then integrate the resulting signal beat-to-beat to recover the original pressure oscillations.

Figure 2:
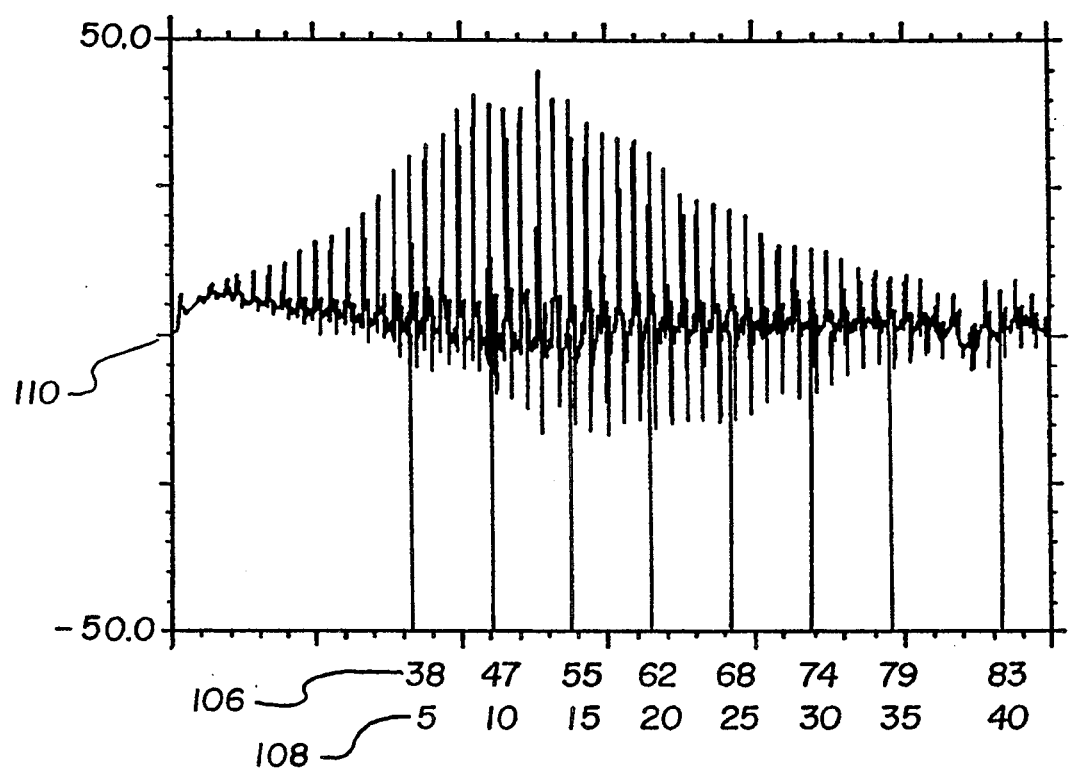
FIG. 2 comprises a graphic plot of the derivative of transducer bladder pressure (dp/dt) as actually recorded from a superficial temporal artery of a patient in a thoracic intensive care unit, as the bladder was inflated from approximately 0 to 90 torr (P cuff).
Figure 3:
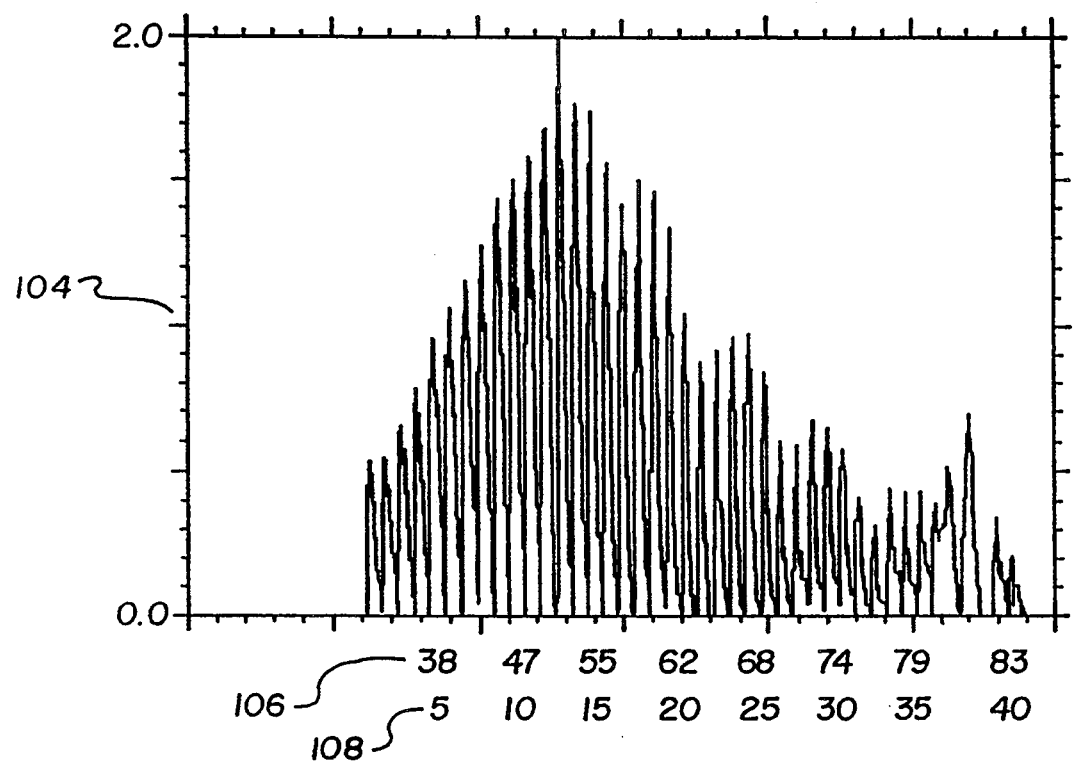
FIG. 3 is a graphic representation of the oscillometric waveform reconstructed from the derivative of the transducer bladder pressure signal represented in FIG. 2.

FIGS. 2 and 3 contain an oscillometric recording from the superficial temporal artery. FIG. 2 is the derivative of the transducer bladder pressure as the transducer bladder was inflated from approximately 0 to 90 torr. The positive offset or bias in the derivative signal corresponds to the slope of the inflation ramp. FIG. 3 is of the oscillometric waveform constructed from the derivative of the transducer bladder pressure signal. Further refinement of the oscillometric waveform is carried out by noting that a single oscillation or beat should start and return to nearly the same diastolic pressure level. Consequently, the sum of the derivative signal over a beat should be zero. Any non-zero sum is assumed to be part of the ramp signal and is subtracted from the derivative signal over the period of the beat. The adjusted derivative signal is integrated over the period of the beat to obtain a more accurate reconstruction of the oscillation or beat. The reconstructed oscillometric waveform is shown in FIG. 4 in its conventional form.

Figure 4:
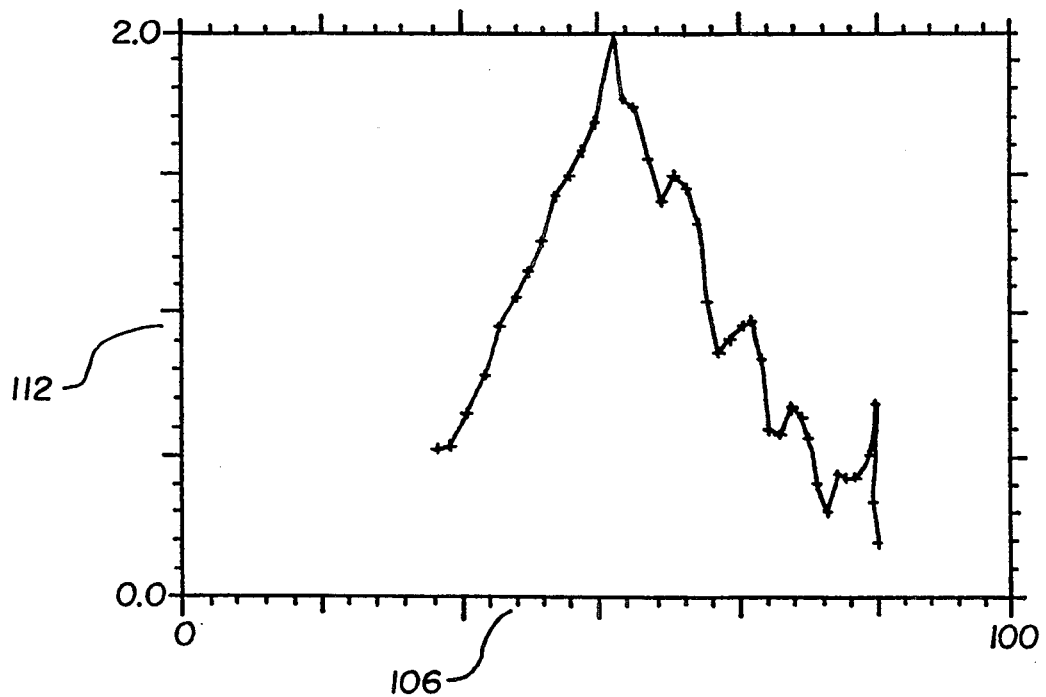
FIG. 4 shows a conventional oscillometric amplitude waveform in graphic display corresponding to the pressure readings represented in FIGS. 2 and 3.

Whereas prior art techniques for estimating diastolic, mean and systolic intraarterial blood pressure involved empirical identification of certain points on the waveform of FIG. 4, the present invention looks at the waveform in its totality. For example, in FIG. 4 the referenced blood pressure attributes could be estimated using prior art techniques by applying software implementations of an 80 percent diastolic algorithm, a maximum amplitude mean algorithm and a 50 percent systolic algorithm. These points represent empirical, and somewhat arbitrary, points on the graph which have been shown to produce close approximations of the blood pressure attributes. As has already been pointed out, however, these are generalizations which may not accurately represent changes in blood pressure, because of differences in age and physiology within the patient. It has now been discovered that processing the signal components and waveform through a neural network not only enhances accuracy of blood pressure determination, but can also be an effective method for reducing or eliminating the effects of noise and artifacts which have previously been processed along with the periodic signals making up the waveform.

Neural networks are based on models of the nervous system and employ adaptive signal processing techniques. Once a neural network is trained, it provides a means of computing an appropriate output signal when presented with a given input signal. Training data are used to modify the neural network weights as applied to various nodes making up the network until the network is optimized in a stochastic sense to provide the appropriate output for a given input.

The present invention introduces an application of neural networks for identification or estimation of physiological parameters which can be estimated by indirect measurements made with respect to the patients body. Such indirect measurements are feasible where a physiological event can be monitored based on generation of a sequence of signals which are quantitatively dependent upon the variable physiological parameter. As has been indicated, blood pressure is a prime example of such an indirect estimation, based on monitoring signals generated in oscillometry.

The neural network can be trained to compute estimates of intraarterial blood pressure from noninvasive oscillometric signals. Because the network processes the entire oscillometric signal rather than trying to identify a single occurrence, such as the point of maximum oscillation, the network is inherently more robust (less sensitive to noise and artifact) than standard oscillometric algorithms. Furthermore, unlike standard algorithms whose accuracy varies with factors such as blood pressure and pulse pressure, the network can provide nonlinear processing of the input signal and thus be relatively consistent over a wide range of pressures.

A neural network may be specified in terms of its architecture. This includes the number of nodes and the interconnection relationships between them, node characteristics such as input/output functions, and learning or training rules which define the method by which the node interconnection are adapted during training. The power of a neural network arises in part from the use of nonlinear functions to process node inputs and the use of parallel distributed processing wherein a given piece of information is not restricted to a single node but may appear as input to many nodes which may operate on the network inputs concurrently.

Figure 5:
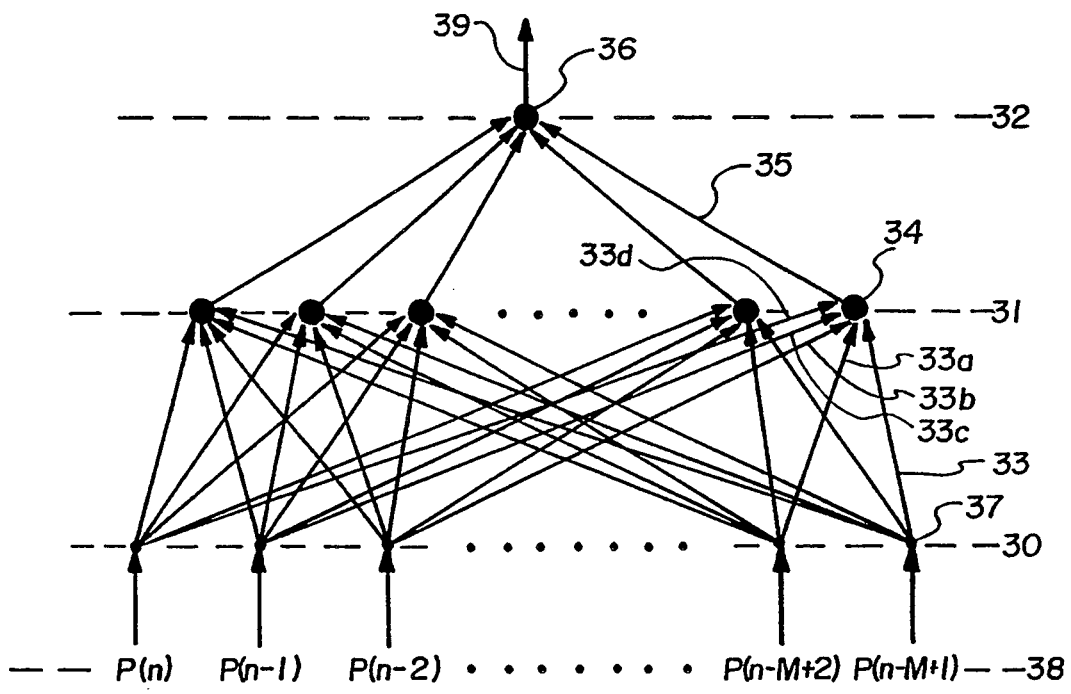
FIG. 5 is a graphic display of a three layer neural network as is used in the preferred embodiment disclosed herein.

A three layer, feed forward neural network was designed to process oscillometric amplitude waveforms with the present invention as shown in FIG. 5. The three layer system includes an input layer 30, one hidden layer 31 and an output layer 32. Although reference is generally made throughout this disclosure to a single output layer it is to be understood that multiple output layers could be implemented where separate and distinct output values are to be developed from the same set of output data. For example, the present invention might embody three outputs representing the respective diastolic, mean and systolic blood pressure values for a single set of inputs from a patient. Accordingly, reference to single output is not to be limited in a restrictive sense, but rather shall be interpreted as meaning at least one output for the network.

Each input node represented by P(n), P(n-1) etc. as set forth in FIG. 5 is connected through a weighted link 33 to every hidden layer node 34. Similarly, each hidden layer node 34 is in turn connected through a weighted link 35 to the single output layer node 36.

With respect to its application for estimation of blood pressure attributes, forty input nodes 37 were provided for the neural network and adapted to receive forty incremental signal samples of a normalized oscillometric amplitude waveform (cuff pressure oscillation amplitude versus cuff pressure). These samples were taken over evenly spaced increments of 4 torr over a cuff pressure ranging from 20 to 176 torr. These forty input samples were stored in computer memory and then concurrently transmitted to the forty input nodes of the input layer 30. In other words, the first sample was transmitted to P(n), the second sample to P(n-1), etc. This total transmitted set of sample signals is concurrently received at the input layer 30 and represents a sample view of the waveform which represents a single blood pressure determination procedure.

This input signal is processed through one or more hidden layers 31 with application of weighting factors at interconnecting nodes to establish an internode relation between the input signals 38 and a desired output signal 39. This processing includes adjustments made within the neural network which at the weighting links 33 and 35 which modify the value of the output signal 39 to match the particular value of the blood pressure or other physiological parameter which is to be determined. This is accomplished in a training sequence wherein the output value 39 is a known value which is generated by virtue of the adjustments made to the input signals 38 as the signals are processed through the network. The process of training the neural network to accomplish this result involves initially establishing appropriate, fixed weighting factors within the weighting links 33 and 35 such that upon occurrence of a similar set of input signals 38 in a future monitoring application of the neural network, an appropriate output signal 39 will be computed by reason of the applied waiting factors within the links 33 and 35 which have been saved in memory. This procedure will be outlined in greater detail hereafter.

Nodes are commonly characterized by an internal threshold or offset and the type of nonlinearity through which the node inputs are passed. The internal thresholds and offsets of the hidden layer nodes 31 are determined adaptively utilizing a well known back propagation algorithm, which is a generalization of the Widrow-Hoff Delta Rule. The backward error propagation algorithm is a gradient descent algorithm designed to minimize the mean square error between the desired output and the actual output of the network. In order to generate an error term, the data set used to train the network must contain not only network inputs, but also the desired output which is specified and used in the supervised training of the network.

Application of the back propagation algorithm consists of the following three steps:

1. Input data is processed forward through the network to generate an output. An error term is computed using the difference between the desired output and the actual network output.

2. The error term is propagated back through the network to modify the internode connection weights and node thresholds so as to minimize the mean square error.

3. Steps 1 and 2 are repeated with new input data in an iterative adaptive process. Commonly, adaptation is halted and the connection weights are saved after the network has reached some specified level of convergence, such as when the error has dropped to 10 percent of the desired output. The following is a representative listing of the equations and steps used in implementing the back propagation algorithm for oscillometric waveform processing.

1. Initialize internode connection weights to small random values.
2. Present training data to the network (i.e. operate network in feed forward mode using input data).
3. Adapt internode connection weights using the network output and the desired output as follows.

Weight Update Equation:

$$w_{ij}(n+1) = w_{ij}(n) + \text{new } e_j(n)x_i(n)$$

$w_{ij}(n)$ is the weight from hidden node i to an output node or from an input node i to a hidden node j at time n.
$x_i(n)$ is either the output of node i or is an input.
new is a gain term, convergence coefficient.
$e_j(n)$ is the error term computed for node j.
Error Term if j is a Hidden Layer Node:

$$e_j(n) = [d_k(n) - y_j(n)][1 - y_j(n)][y_j(n)]w_{kj}(n)$$

Error Term if k is an Output Layer Node $$e_k(n) = [d_k(n) - y_k(n)]$$

$x_j(n)$ is the output of hidden layer node j k is over the output nodes.
4. Repeat starting at step 2.

Figure 6:
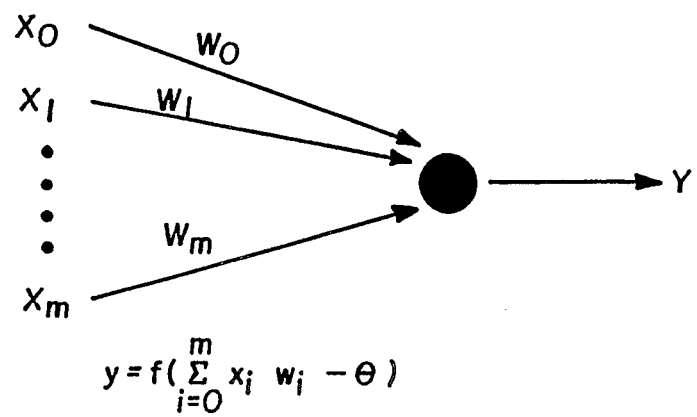
FIG. 6 is a graphic representation of a node input/output function.

For each hidden layer node 34, the weight of the sum of the inputs 33, 33a, 33b, 33c and 33d (dot product of the node input and weight factor) were passed through a sigmoid nonlinearity of the form shown in FIG. 6. Because a continuous output reading of arterial blood pressure in torr was desired from the neural network, the sigmoid nonlinearity was not applied to the output layer. Instead, the output layer node functions as a simple summer of the weighted outputs of the hidden layer nodes. The sigmoid nonlinearity used in the hidden layer nodes is of the following mathematical form:

$$f(a_j) = \frac{1}{1 + e^{-(a-\Theta)}}$$

Figure 7:
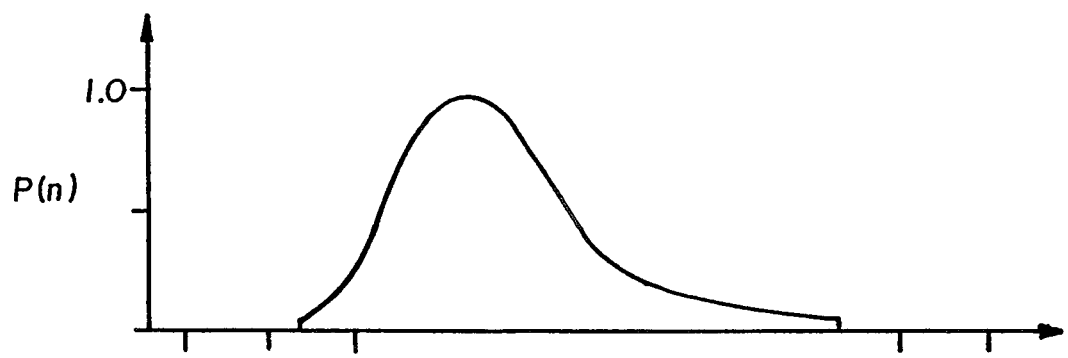
FIG. 7 provides a graphic illustration of a normalized oscillometric amplitude waveform developed from a sampling of signals at 4 torr increments.

The input of the forty samples to the network input node layer 30 is represented by a normalized oscillometric amplitude waveform as shown in FIG. 7. This amplitude waveform is part of the inventive process wherein the sequence of signals generated by the cuff and pressure transducer are sampled at 4 torr intervals to supply a set of forty-plus sample signals representing the total range of pressures covered by the blood pressure determination procedure. With respect to each sample signal, a feature is identified which constitutes the maximum amplitude of that sample signal. This same process could be applied to other monitoring procedures which involve oscillatory signals having an amplitude feature. This feature is then utilized to develop the referenced waveform in FIG. 7 wherein the respective sample amplitude values form a locus of points representing the amplitude of cuff pressure over the blood pressure determination. This waveform is the image or pattern corresponding to an actual blood pressure value as it is represented at the forty input nodes of the neural network. The neural network is trained to compute the actual blood pressure value from this waveform and present it at the output layer upon receipt of a similar set of input signals.

Based on the foregoing description and FIG. 1, the general device for implementing the training and use of a neural network with respect to variable physiological parameters for measurement can be summarized as follows. The device includes a sensing means 20 for indirectly detecting changes in a physiological parameter which is to be quantitatively monitored and estimated. Selection of the sensing means will depend on the nature of the parameter and will generally be a conventional monitoring which is already being used to attempt such estimations.

As has been indicated, a blood pressure cuff which currently generates oscillometric signals forms the sensing means for the blood pressure application. Pulse oximetry is another monitoring procedure which may be adapted for processing with a neural network. In this case, an estimation of blood oxygen saturation is transmitted through or reflected from body tissues. A third area of application is generally referred to as dilution cardiac output. This monitoring procedure estimates cardiac output or blood flow by processing the time dependent concentration or temperature signal produced by injection of a dye or thermal solution into the vascular system. Obviously, in the latter two cases different sensing devices will be utilized, and an appropriate signal, which is quantitatively dependent upon the variable physiological parameter, but which is not suitable for providing direct quantitative readout based on direct measurement of that parameter.

The sensing means and an associated signal generating means 23 together cooperate to produce the required set of signals to be applied at input nodes in the neural network. The neural network includes a supporting computer system 21 coupled to the generating means and operates to control data collection, processing and display. It will be apparent to those skilled in the art that reference to the computer system would include other data processing devices such as hardware analog circuits or integrated circuits which could be specifically designed to implement a neural network without a separate computer system.

The neural network has been described in one preferred embodiment, and can generally be described as including (i) a series of input nodes for receiving signals from the generating means, (ii) a series of hidden nodes coupled individually to each of their respective input nodes, and (iii) at least one output node which is coupled to each of the respective hidden nodes for supplying a desired output value. The neural network includes means for generating the single output signal from the signals received at the input nodes wherein the output signal provides the trained estimated value of the physiological parameter.

The computer system also operates as a data storage means for storing training data generated within the neural network with respect to relationships between the input signals and desired values for the physiological parameter to be designated during such training and supplied as an output. The computer system may also provide a readout means for indicating the estimated value of physiological parameter based on the output signals from the neural network.

When used as part of a training system, the present invention also includes direct detection means which are coupled to the computer system and adapted with means for determining an actual, true value for the physiological parameter. This direct detection means is applied concurrent with receipt of sample signals received from the generating means. Memory storage means is provided in the computer system for storing parameter true values in association with corresponding input signals fed to the neural network.

Although the number of input nodes will vary depending on the number of input signals to be processed, or at least two input nodes are required to establish a minimum statistical image. Likewise, hidden nodes will differ in number and in levels. A single hidden layer will generally be adequate and will usually include at least two nodes making up the single hidden layer between the input nodes and the single output node. Where additional boundary conditions within the neural network are required, multiple hidden layers may be applied.

The computer also provides a selection control means for sampling periodic signals generated from the generating means. As indicated in the previous example, forty sample signals were taken over the blood pressure monitoring procedure pressure range and were placed in memory for subsequent transmission on a concurrent basis to the input nodes of the neural network. Generally, at least one feature will be identified within these sample signals, which feature can be processed through the neural network as a feature signal having a dependent relationship with respect to the physiological parameter.

Where the inventive system is used in a training mode, a portion of computer memory or other memory means is set aside to store training data including weighting factors and parameter values which can be used to generate a value for the physiological parameter including mean intraarterial blood pressure, systolic intraarterial blood pressure and diastolic intraarterial blood pressure. When the present invention is applied to a monitoring application, the invention need not include either connection with the invasive detection means required for determining the true value for the physiological parameter or recorded training data. Instead, the device need only include the trained neural network and interconnection weights necessary to determine neural network output estimates of the desired physiological parameter from the on-line data input. In this monitoring configuration, the device may include three separate neural networks respectively configured and trained to determine the named blood pressure attributes, or may be a single neural network with three outputs configured to generate the same result. Further detail with respect to technical implementation of the neural network in accordance with the teachings of this invention is unnecessary in view of current knowledge of those skilled in the art with respect to neural network systems generally.

Figure 8:
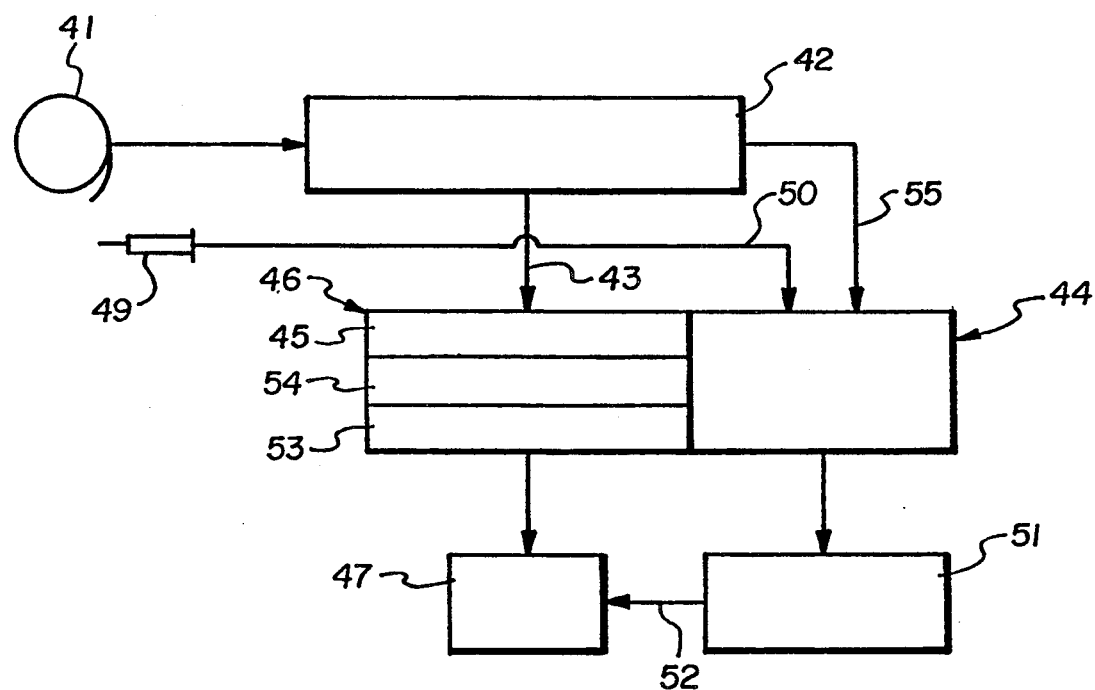
FIG. 8 represents a block diagram illustrating the training phase and methodology for applying a neural network for determining physiological parameters in accordance with the present invention.

FIG. 8 represents the general procedural steps associated with the present invention in its broader terms. The first step involves identifying the physiological parameter to be quantitatively monitored and estimated. Item 41 represents a blood pressure cuff and the associated physiological parameters of diastolic, mean and systolic blood pressure. The cuff 41 also represents the associated hardware to support operation of the cuff in its conventional manner. The next step involves generating a sequence of signals 42 which are quantitatively dependent upon the variable physiological parameter, but which are not suitable for providing a direct quantitative readout based on direct measurement of the parameter. The third step comprises transmitting these signals to and processing such signals within a computer system 44, including input nodes 45 of a neural network 46 supported by the computer system 44 is similar to that described previously and provides capability of generating a single output signal 47 for the combined input signals 43. This output signal 47 provides the estimated value of the physiological parameter corresponding to the referenced input signals 43.

In the training mode, the device represented by FIG. 8 includes steps for determining the actual, true value of the physiological parameter concurrent with the generation of signals as represented by item 42. This procedure is represented by an intravenous device 49 which is invasively positioned within the patient to directly readout actual blood pressure values for transmission along line 50 and to the computer system 44. This true value for the parameter is processed by the computer system and stored as training data 51. This value is transmitted via line 52 as the desired output value 47. Adjustments are then made within the neural network 46 which modify the value of the signal transmitted from the output nodes 53 to a value which equals the desired output value 47 transmitted from training data 51. Typically this is accomplished by applying weighting factors at interconnecting nodes within the neural network between the input nodes and hidden layer of nodes 54 and between the hidden layer of nodes 54 and the output node 53.

During the training phase, the input signals 42 are presented to the neural network, along with the adjusted weighting factors required to modify the input signal through the hidden layer to reach an output value equal to the output value generated by the invasive measurement 49. These data are collectively recorded as training data 51 and used to train the neural network. After training, the neural network can be used for on-line monitoring of a patient's blood pressure in the absence of the invasive measurement.

This series of steps is repeated a sufficient number of times to train the neural network to recognize relevant input signals and estimate the value of the desired physiological parameter based on association of on-line input signals at some future time.

As indicated previously, this method is particularly applicable with respect to oscillatory signals which generate a waveform corresponding to a single monitoring procedure. In the present case, this diagnostic test procedure is represented by the sequence of a blood pressure cuff and implementing conventional oscillometry to generate the desired sequence of signals. To be useful in such a system, it is desirable that the oscillatory signals be changing in amplitude or frequency in a dependent relationship with respect to the physiological parameter. This enables the neural network to learn the various relationships through actual training wherein the true value of the parameter is taught to the neural network in association with the input signals received.

An additional value of utilizing a neural network is its ability to analyze and interpolate from several sample signals and generate an accurate estimation of the parameter value without having the need to process the full sequence of signals originally generated 42. In accordance with this method, the computer system or other form of selection control means selects a plurality of sample signals from the sequence of signals 42 which may be received directly through line 55. The computer system identifies at least one feature, such as signal amplitude, within the sample signals which can be processed through the neural network as a feature signal. The normalized oscillometric amplitude waveform illustrated in FIG. 7 demonstrates how 40 signals selected at 4 torr increments can generate a typical waveform without the need for processing all signals as is represented in the waveform illustrated in FIGS. 3 and 4. The subject inventors have successfully developed accurate results in a blood pressure monitoring system by selecting only 3 sample signals and by processing those sample signals through the neural network in accordance with the teachings of this invention. Obviously, at least two sample signals will be required to generate a meaningful waveform, depending upon the training capacity of the neural network with respect to the desired parameter. Accordingly, the neural network system provides a much improved efficiency in that the processing and association steps of analysis can be accomplished with several signals, rather than the full range of designated signals. Generally the selected number of sample signals determining the minimum number of input nodes required with respect to the neural network.

In the preferred embodiment, the specific method of practice involves developing a waveform for each single parameter estimation procedure wherein the predetermined number of sample signals corresponds approximately to the number of input nodes in the network. The sequential signals are stored in memory and are collectively and concurrently transmitted to the input nodes of the neural network as a representative waveform.

Application of the inventive steps represented in FIG. 8 to a specific training session for generating blood pressure training data is accomplished in the following specific format. Specifically, a sequence of oscillometric signals are generated from a pressure sensing means. This means, represented by the blood pressure cuff 41 of FIG. 8, is coupled externally to a patients anatomy in a sensing proximity to a heart pulsing sensing location. The computer system 44 is adapted to identify a set of sample signals at defined increments wherein the primary feature of the oscillometric signal constitutes pulse amplitude. The process continues by measuring and recording pressure values within the pressure sensing means, along with the corresponding pulse amplitude signals described in the previous step. As is represented by item 49, invasive blood pressure measurements are made concurrent with the generation of the oscillometric signals representing heart pulse. This true value is transmitted to the computer system for recording as part of the training data 51. At the same time, the sample feature signals representing pulse amplitude are transmitted to the input nodes 45 for processing through the neural network. Appropriate adjustments are made with application of weighting factors to force the output signal of the network to more closely match the desired output value determined invasively. Repetition of this training continues until the neural network is capable of recognizing sets of input signals and determining accurate estimates of blood pressure values.

When applied with respect to oscillometric techniques, the typical range of measuring and recording pressure values extends over defined increments from approximately 20 to 200 torr. The subject inventors have found an appropriate increment to be 4 torr, representing approximately 40 to 45 sample signals.

The present system was tested with respect to five dogs. A total of 425 recordings of oscillometric amplitude waveforms, along with simultaneous invasive measurements of arterial diastolic, mean and systolic blood pressures were obtained (approximately 85 recordings per dog). Three separate neural networks were utilized, one each for estimating diastolic, mean or systolic blood pressure. These systems were trained utilizing the back propagation algorithm as previously discussed.

The networks were trained and tested using a train-on-4/test-on-1 procedure. Following training of the network on data from 4 of the dogs, adaptation of the internal hidden layer thresholds and network internode connection weights was halted and data from the fifth dog was processed forward through the network to obtain estimates of either arterial diastolic, mean or systolic blood pressure. The protocol was repeated five times such that data from each dog was tested on a network trained using data from the other four dogs.

Since no clear rules exist for determining the optimum number of hidden nodes, the training and testing process was repeated using 3, 7, 15, 31, and 63 hidden layer nodes in each network. The convergence coefficient which appears in the equations of FIG. 6 was set to equal 0.001. respectively. Training data was passed adaptively through each network a total of 1,500 times. Following each adaptive pass, the training data (340 oscillometric readings from 4 dogs, 85 readings per dog) was processed forward through the neural network to evaluate the level of convergence. The test data from the fifth dog (85 oscillometric recordings) was then processed forward through the network to evaluate neural network performance at different levels of convergence. The convergence coefficient, and total number of passes through the training data were selected to yield reasonable rates of convergence, final convergence levels, and steady state oscillations.

The level of convergence was quantified in terms of the mean error, the standard deviation of the errors and the mean square error. The error was computed as the difference between the desired (invasive arterial blood pressure measurement) and the actual network output (noninvasive estimate). The mean square error is the variable which the back propagation algorithm is attempting to minimize and thus serves as an appropriate measure of the level of convergence.

Network performance on the test data was also evaluated in terms of the mean difference and standard deviation of the differences between arterial measurements and the noninvasive neural network estimates of arterial blood pressure. Conventional oscillometric algorithms were also used to obtain estimates of arterial blood pressure. Mean blood pressure was estimated as the cuff pressure at which the oscillations first reached their maximum. Systolic blood pressure was estimated as the cuff pressure at which the oscillations had decreased to 50 percent of their maximum amplitude. Diastolic blood pressure was estimated as the cuff pressure at which the oscillations had increased to 80 percent of their maximum amplitude.

Figure 9:
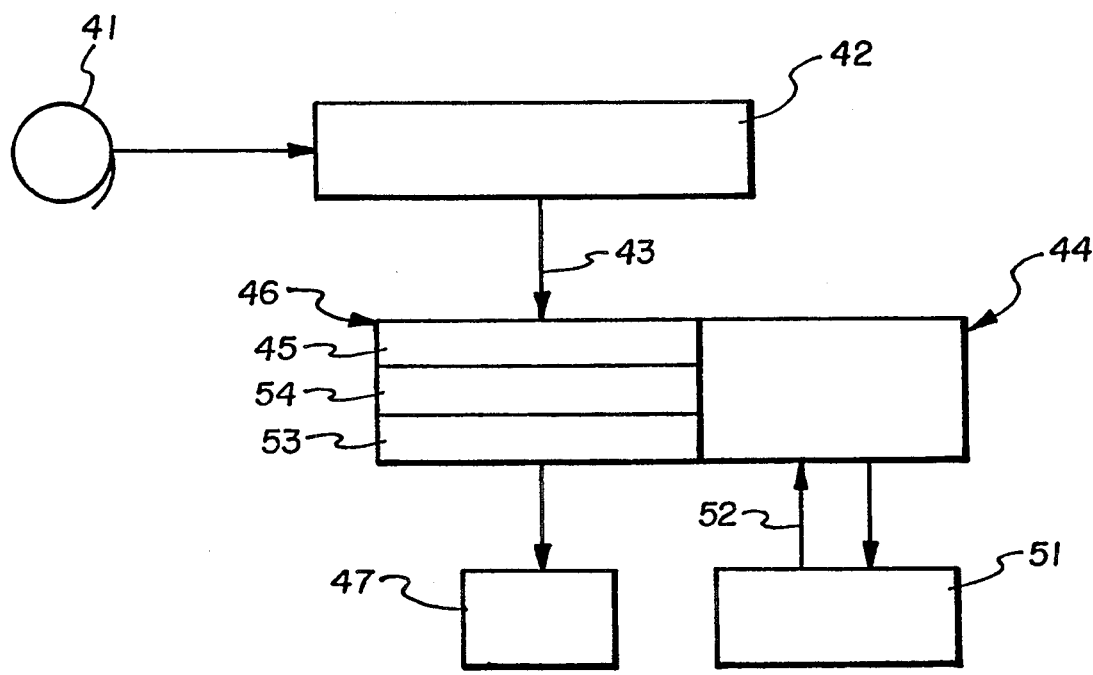
FIG. 9 represents a monitoring (nontraining phase) application of the present invention operable to generate output values estimating the physiological parameter.

Use of the present system in the application phase, as contrasted with the training phase, is represented in FIG. 9. The methods of processing input signals through the neural network are substantially the same as those used during the training phase; however, no concurrent measurements of an invasive nature are made nor are modifications of the network made, since the purpose of the application of weighting factors is to estimate such parameters without the discomforts and trauma of more difficult or invasive techniques.

In summary, this method of quantitative estimation of the variable physiological parameter is practiced by identifying the parameter to be estimated, generating a sequence of on-line signals which are quantitatively dependent upon the variable parameter, and transmitting those signals to the input nodes of the neural network. At this stage, the neural network has been appropriately trained to identify the closest parameter value based on weighting factors which have been modified as part of the training process. Actual output values are obtained by processing the on-line signals within the neural network with generation of an output value corresponding to such input signals. In view of the fact that those skilled in the art will readily understand the methodology of this application phase as compared to the training phase earlier described, duplication of that earlier description is deemed unnecessary. Indeed, the foregoing description is incorporated herein by reference as it relates to processing on-line input data through the neural network and generating an estimated output value for the blood pressure or other parameter based on comparison and interpolation by the neural network as is enabled through its training data.

FIGS. 10a, 10b and 10c disclose examples of learning curves obtained by processing the training data forward through the network after each adaptive pass. This data corresponds to a network having three hidden layer nodes. FIGS. 11a, 11b and 11c contain corresponding performance curves obtained by processing the test data forward through the same neural network having 63 hidden layer nodes. These figures represent training data which was presented within the network a total of 5,000 times, as opposed to the earlier mentioned 1,500 presentations.

As shown in FIG. 10a, 10b and 10c, the mean error learning curves change rapidly at first, sometimes changing sign and then begin the slow noisy ascent or descent toward 0. Both a standard deviation of the errors and the mean square error are characterized by noisy decaying exponentials. The rate of convergence was found to decrease with an increase in the number of hidden layer nodes. However, the mean error, the standard deviation of the errors, the mean square error, and the steady state oscillation also decreased with an increase in the number of hidden layer nodes.

As shown in FIGS. 11a, 11b, and 11c, performance curves are generally of the same form as the corresponding learning curves. (FIGS. 10a, 10b and 10c). However, although the mean difference approaches zero with increased training, the standard deviation of the differences may actually increase. Thus, increasing the level of convergence or reducing the mean square error during training does not necessarily insure better performance on test data. A possible explanation for such an effect is that the network becomes specific to the training data and loses its ability to generalize.

In summary, although the convergence patterns vary depending on the number of hidden layer nodes and the number of passes through the training set, the different neural network architectures all successfully converged. In general, increasing the number of hidden layer nodes was associated with a higher level of convergence on the training data and improved performance on the test data in the form of decaying exponentials. Increasing the number of hidden layer nodes was also associated with smaller steady state oscillations in both the learning and performance curves. Increasing the number of passes through the training data was associated with a higher level of convergence; however, this did not always translate into an increase in performance on test data, particularly after prolonged training. The price for improved performance is an increase in the number of interconnections and thus the amount of time required to train or process data through the network.

FIGS. 12a, 12b, 12c and 13a, 13b, 13c show, respectively, the differences and the standard deviation of the differences between the invasive measurements and the noninvasive neural network estimates of arterial blood pressure plotted against the number of hidden layer nodes. The network's performance was evaluated at different levels of training by processing test data forward through the networks after 50, 250 and 1,500 adaptive passes through the training data. Both the mean difference and the standard difference FIGS. 12a, 12b and 12c and the standard deviation FIGS. 13a, 13b and 13c of the differences tended to decrease as the number of hidden layers was increased. The improvement in performance was in the form of a noisy decaying exponential. As previously noted, increased training did not necessarily ensure better performance. The best performance (minimum standard deviation of the differences) in estimating diastolic, mean or systolic blood pressure was achieved using networks with 63 hidden layer nodes (the maximum number of hidden layer nodes tested). For diastolic estimates the best performance was achieved after 422 training passes; for mean estimates, after 18 training passes; and for systolic after 548 training passes.

In comparison with conventional algorithms used for determining blood pressure parameters the neural network oscillometric blood pressure estimator performed as well or better based on data obtained from the 5 dogs. The neural network approach for estimating blood pressure and other physiological parameters provides a potentially powerful alternative to the conventional algorithmic processing of oscillometric amplitude waveforms. One advantage arises because the neural network does not require detailed knowledge of the relationship between the input (oscillometric waveform) and the output (arterial blood pressure attributes). Instead, the neural network develops through supervised training, an internal set of rules used to transform or map inputs into the appropriate outputs. An additional, major advantage of neural networks is that they are very simple to implement. Once the neural network is appropriately trained, it can readily respond with generation of appropriate parameter estimations. In addition, the neural network system has a natural robustness in that it is not as sensitive to artifact and noise as conventional algorithmic processes. Unlike conventional algorithms, which usually depend on the identification of a single event (e.g., the lowest cuff pressure at which maximum oscillations occur), the entire oscillometric waveform can be processed by the neural network to obtain an estimate of the desired blood pressure attributes.

Figure 14:
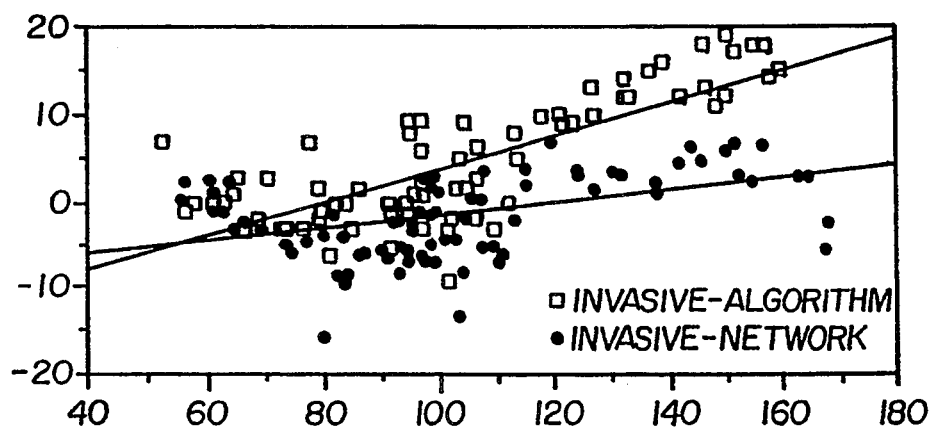
FIG. 14 illustrate numerical data and corresponding graph data comparing the conventional algorithm processes, neural network processes of the present invention and invasive measurements for diastolic, mean and systolic blood pressure.
Figure 12A:
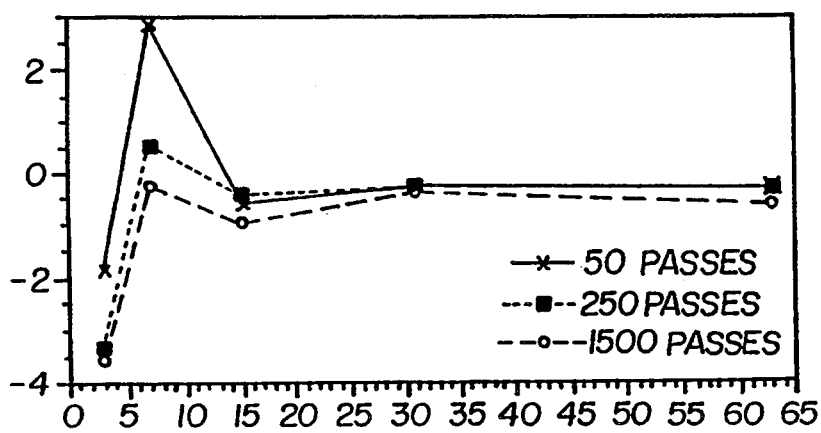
FIGS. 12a, 12b and 12c provide a graphic representation of neural network performance after 50, 250 and 1,500 passes through the training data plotted against the number of hidden layer nodes. The neural network performance in these graphs is evaluated in terms of mean difference between invasive measurement and neural network estimates.
Figure 12B:
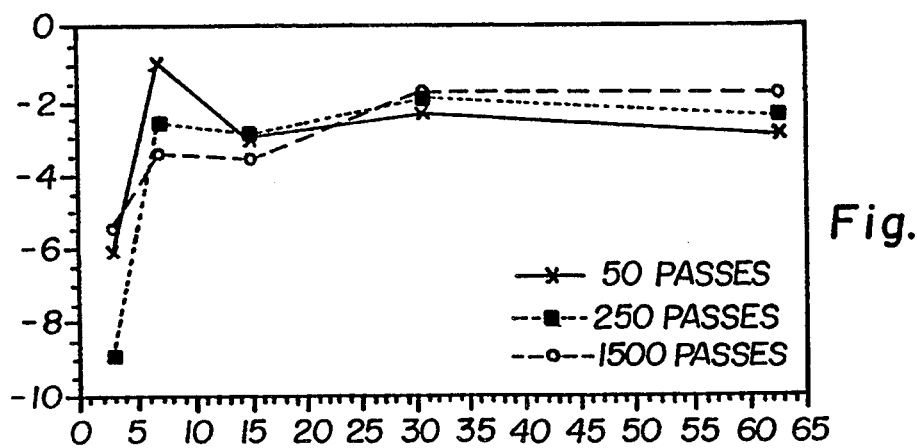
Figure 12C:
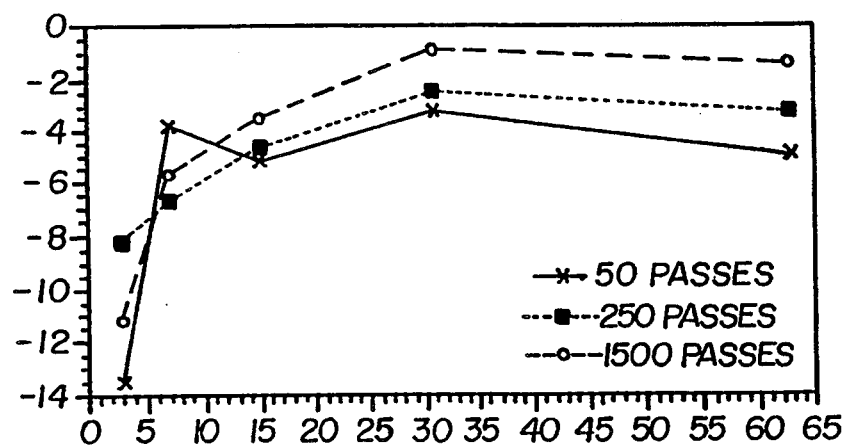
Figure 13A:
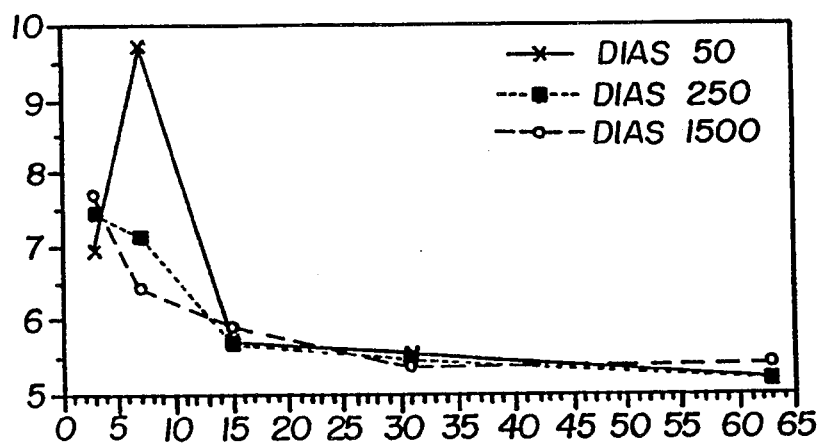
FIGS. 13a, 13b and 13c provide similar graphic representations as represented in FIGS. 12a, 12b and 12c, except that the performance is evaluated in terms of the standard deviation of the differences between invasive measurements and neural network estimates.
Figure 13B:
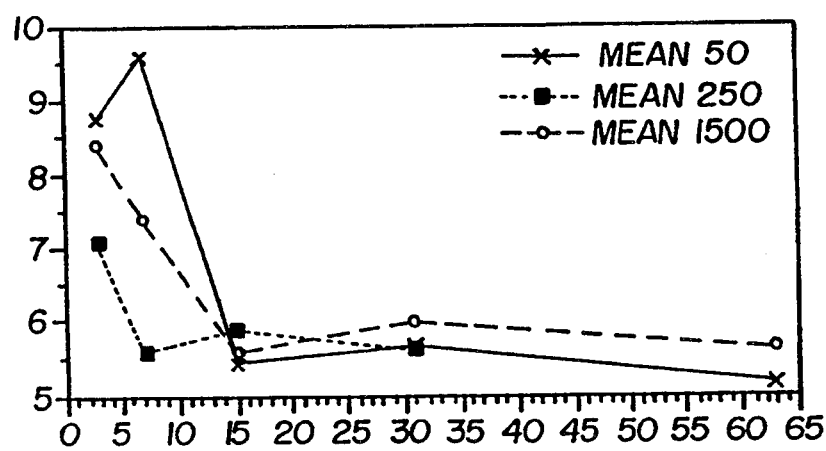
Figure 13C:
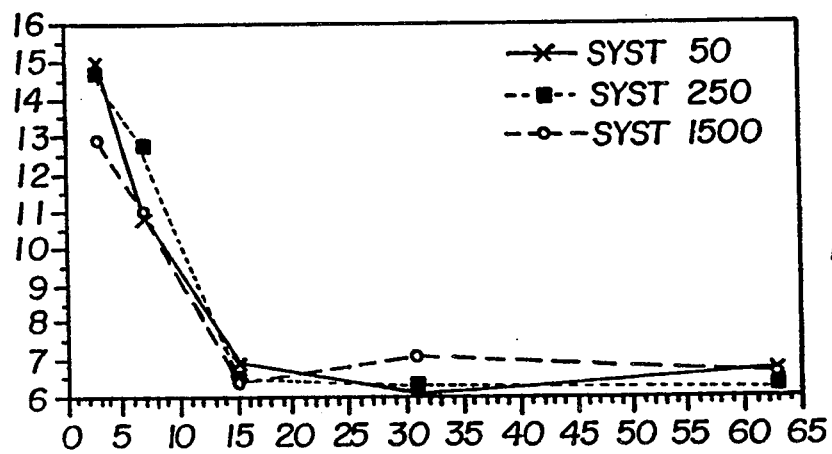

The favorable results of the present invention as compared to conventional algorithm techniques are generally summarized in FIG. 14. This figure discloses a table of values comparing invasive measurements with conventional algorithm techniques, as well as the neural network system of the present invention. The first row in the table contains the mean differences, plus or minus the standard deviation between invasive measurements and noninvasive conventional algorithm and neural network estimates of blood pressure. These statistics were computed using the data generated with respect to the test animals previously described. The second row contains the means and standard deviations for each dog, demonstrating improvement with respect to intrasubject variations. The attendant graph provides a more dramatic example of how the accuracy of the conventional algorithm decreases with increasing blood pressure while the accuracy of the neural network remains relatively constant.

Accordingly, it is apparent that the distributed and nonlinear processing capabilities of a neural network system as disclosed herein offers significant advantages and potential for maintaining the accuracy of blood pressure estimates over a wide range of physiological conditions.

The neural network may also be utilized as part of a pre-classification system for identifying the nature of certain input signals. For example, when a set of input signals arrives at the input nodes of a neural network, certain patterns may be readily detectable which are unique to a child as opposed to an adult patient. Such a pre-classification application is useful for identifying various patient conditions which fall in broad categories generally identified as patient induced conditions. Age, body size, disease conditions and other conditions falling within other unique classifications can be detected by certain patterns which are reproduced at the input nodes of the neural network. Once detected, the neural network can then reduce the processing of such information by restricting the selective training data to that applicable for the selected classification.

As an example, a neural network may be trained to recognize blood pressure attributes as they relate to pediatric patients. By using a pre-classifier, the neural network can immediately recognize that the input signals have a pediatric pattern, thereby limiting comparison of input data with training data specifically developed for pediatric patients. Similar applications of the neural network can be utilized in this pre-classification rule for equipment induced conditions that may represent a malfunction. Reference to training data which enables the neural network to recognize certain common malfunction conditions for monitoring equipment can lead to more timely alert of attending medical personnel for equipment correction or maintenance.

In a similar manner, the neural network of the present invention can be trained to recognize noise and artifact input received at the input nodes of the neural network. This technique was specifically applied with respect to measurement of test animals as previously described. These specific procedures involved a initial determination of the oscillometric waveform quality based on human observation of the waveform graph. This was accomplished by observing the waveform and noting the occurrence of noise or artifact signal and then assigning a "quality" factor such as "excellent", "good" or "artifact". Training samples from a total of 245 waveforms were selected and processed through a neural network having 60 input nodes, 15 intermediate hidden nodes and a single output. This network was trained using a supervised stochastic method to calculate a "quality" number at the output node based on this goodness indicator. In actual experiments, the numbers selected were 500 representing an excellent waveform, 0 representing a good waveform and −500 indicating an artifact. At the end of the training the network was consistently able to calculate lower numbers for the artifact waveform and higher numbers for the good and excellent waveforms. It was thus able to distinguish the worst quality waveforms from the better ones, enabling the network to thereby distinguish and reject artifact and noise signals. This held true for both the training data set and the nontraining data set of signals. It was also noticed that when this procedure was tested on the nontraining data set, the network properly classified a few waveforms which had been misclassified during the initial human classification process.

Figure 15:
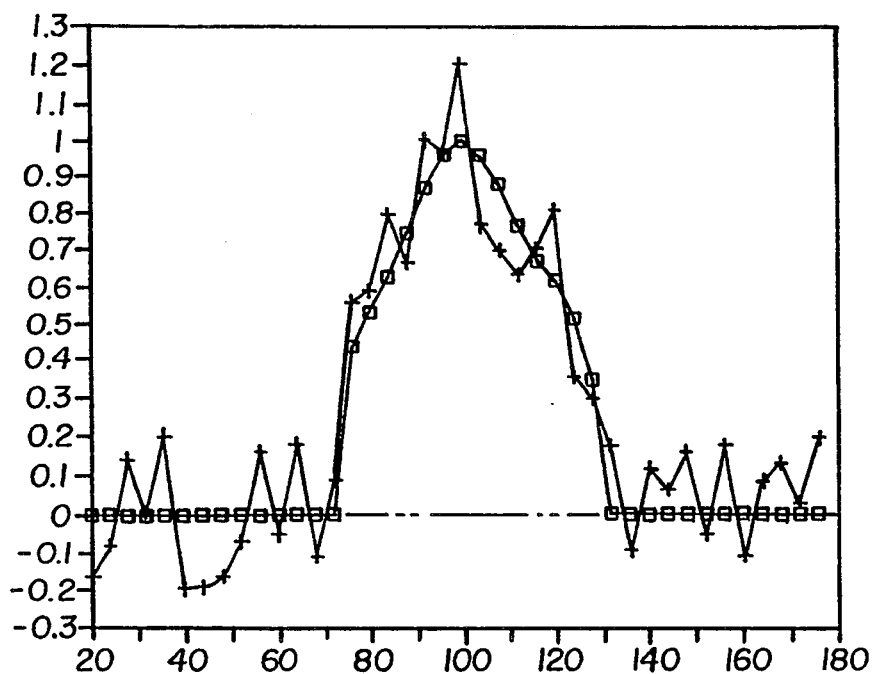
FIG. 15 graphically compares a clean signal with a superimposed signed including random noise.

FIG. 15 presents a graph which illustrates normal oscillometric pulse amplitude versus cuff pressure. The quality or clean signal is represented by the small square box point indicators, whereas the random noise or artifact signal is superimposed and indicated with + signs. Processing of these respective signals confirms the ability of the neural network to distinguish and reject inappropriate signals and record and process quality signals.

Figure 16:
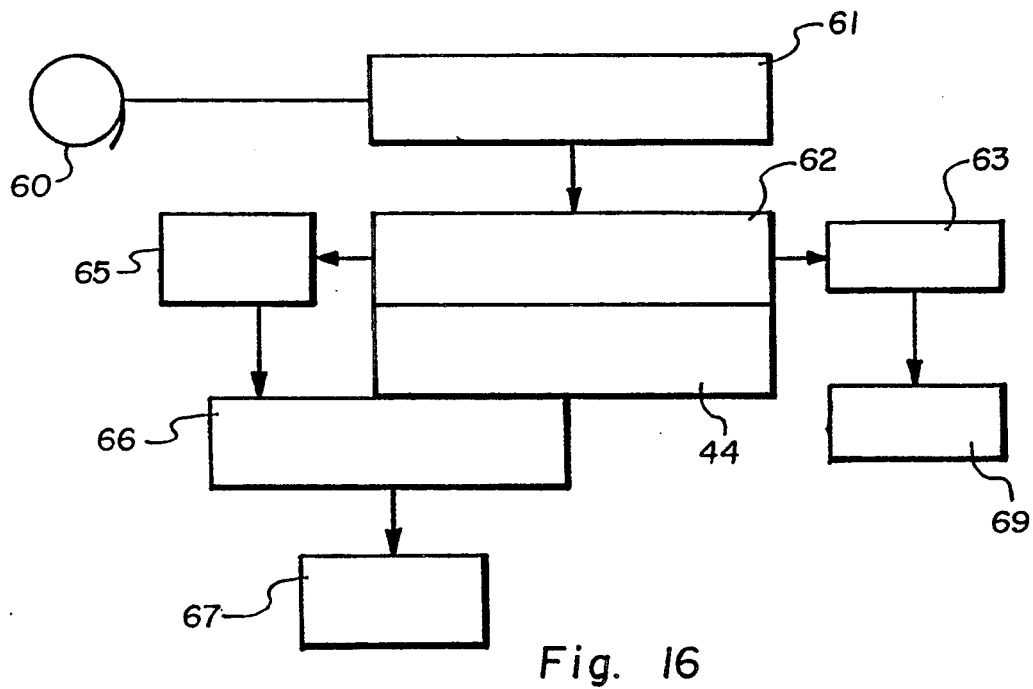
FIG. 16 illustrates in block diagram a neural network adapted for pre classification and rejection of artifacts.

This latter function of pre-classification is represented in FIG. 16. Here again, the selected parameter is a blood pressure value generated by use of an oscillometric system represented by a cuff 60. A sequence of signals are generated 61 and transmitted to a pre-classification neural network 62. In this case, the pre-classification network is trained to recognize signals which are corrupted by extraneous noise and to classify these as artifacts 63 which will be rejected or stored as training data for future recognition. All other signals are considered to be of good or excellent quality and are transmitted to the neural network as previously described 66 for processing and estimation of blood pressure as an output signal 67.

Development of training data is accomplished in a procedure similar to that outlined with respect to training of the neural network to recognize certain blood pressure parameter values. Typically the signal input is classified as corrupted or artifact and weighting factors are applied at interconnecting nodes within the neural network 62 to establish an internode relationship between the corrupted signal received at the input nodes and a desired output signal which is defined to be an artifact 63. These relationships and values are saved in computer memory for a future association with respect to signal input which is not predefined with respect to quality.

During training processing for the blood pressure neural network the pre-classification neural network 62 may be useful for identifying and discarding noise and artifact signals such that these are not used as training data. This operates to enhance the accuracy of the training data stored as much as all artifact and noise signals are pre-classified and rejected. In this case, training data which is being coordinated with the output signal of the blood pressure neural network 66 is of pure value, overcoming a major cause of error in conventional algorithm processing which comprehends both quality and artifact signals on an equal basis.

It will be apparent to those skilled in the art that the various examples presented in this disclosure are representative and are not to be considered as limiting with respect to the following claims.

We claim:

1. A method for on-line calculation of a variable physiological parameter of a patient, said method comprising the steps of:
   (1.1) identifying the physiological parameter to be quantitatively monitored and estimated;
   (1.2) coupling at least one sensor to the patient, said sensor being responsive to register changes in the physiological parameter, which changes are quantitatively dependent on a particular value for the parameter;
   (1.3) activating the sensor to generate a sequence of on-line signals which register changes in the physiological parameter;
   (1.4) transmitting the on-line signals as input signals to a computer system, including input nodes of a neural network supported by the computer system, which neural network is capable of calculating an output signal corresponding to a parameter value from the on-line, input signals;
   (1.5) processing the input signals within the neural network to convert the sequence of input signals to an on-line output signal corresponding to a parameter value by applying fixed weighting factors to the input signals;
   (1.6) generating said fixed weighting factors by retrieving weighting factors which were previously generated by applying a training algorithm with respect to previously collected training data comprising neural network input signals and corresponding known parameter values.

2. A method as defined in claim 1, further comprising the steps of:
   (2.1) selecting a plurality of sample signals from the sequence of signals for processing through a neural network which has been trained to associate such sample signals with a related value for the physiological parameter; and
   (2.2) identifying at least one feature within the sample signals which can be processed through the neural network as a feature signal.

3. A method as defined in claim 2, wherein step 2.2 includes the step of identifying amplitude of oscillatory signals as the feature which defines the feature signal, said method further including the step of developing a waveform based on the sequential signals generated in step 1.3, said waveform being represented by the locus of points representing the amplitude of each oscillatory signal graphed with respect to a measurement of blood pressure over a time period comprising a single measurement procedure.

4. A method as defined in claim 3, wherein step 2.2 comprises the more specific step of selecting at least two sample signals from all signals generated pursuant to step 3 for the single measurement procedure and processing the amplitude feature signal of these sample signals in accordance with the remaining steps of claim 1 to estimate the parameter value without processing all signals being generated.

5. A method as defined in claim 3, wherein steps 1.3 and 1.4 include the more specific steps as follows:
   (5.1) developing a waveform for each single measurement procedure comprising a predetermined number of sample signals, which number corresponds approximately to the number of input nodes existing in the neural network;
   (5.2) storing in memory the sample signals; and
   (5.3) transmitting the stored sample signals of the waveform to respective input nodes of the neural network.

6. A method as defined in claim 5, wherein step 5.1 comprises the more specific step of selecting at least two sample signals from all signals generated pursuant to step 1.3 for the single measurement procedure and processing the amplitude feature signal of these sample signals in accordance with the remaining steps of claim 1 to apply on-line signals at the neural network to calculate the estimated parameter value by sampling only several representative signals from the sequence of signals being generated.

7. A method as defined in claim 2, comprising the more specific step of identifying the physiological parameter for monitoring and estimation to be a blood pressure parameter selected from the group consisting of diastolic, means, and systolic intraarterial blood pressures.

8. A method as defined in claim 7 for estimating blood pressure parameters, including the additional steps of:
   (8.1) generating a sequence of oscillometric signals representing heart pulse from a pressure sensing means coupled externally to a patient's anatomy in sensing proximity to a heart pulse sensing location; and
   (8.2) identifying the feature within the oscillometric signals to be pulse amplitude.

9. A method as defined in claim 8, comprising the more specific step of measuring and recording pressure values at predetermined increments over pressure ranges from approximately 20 to 200 torr.

10. A method as defined in claim 8, including the more specific step of selecting less than all generated signals of step 8.1 for transmittal to the input nodes of the neural network.

11. A method as defined in claim 10, comprising the more specific step of selecting a representative sampling of at least two generated signals, thereby estimating the waveform developed by the signals transmitted to the input nodes of the neural network without requiring processing of all signals through all interactive nodes of the neural network to generate the desired output signal corresponding to the value of the blood pressure parameter.

12. A method for on-line calculation of a variable physiological parameter of a patient, said method comprising the steps of:
   (12.1) identifying the physiological parameter to be quantitatively monitored and estimated;
   (12.2) coupling at least one sensor to the patient, said sensor being responsive to register changes in the physiological parameter, which changes are quantitatively dependent on a particular value for the parameter;
   (12.3) activating the sensor to generate a sequence of on-line signals which register changes in the physiological parameter;
   (12.4) transmitting the on-line signals as input signals to a computer system, including input nodes of a neural network supported by the computer system, which neural network is capable of calculating an output signal corresponding to a parameter value from the on-line, input signals;

(12.5) processing the input signals within the neural network to convert the sequence of input signals to an on line output signal corresponding to a parameter value in accordance with the following substeps:

12.5a) processing the input signals within the neural network through at least one neural network layer having at least one node by applying fixed weighting factors to the input signals;

12.5b) generating said fixed weighting factors by retrieving fixed weighting factors which were previously determined by applying a training algorithm with respect to previously collected training data comprising neural network input signals and corresponding known parameter values to generate said fixed weighting factors;

12.5c) for each input signal of each node within the neural network layer, calculating a product of the input signal and fixed weighting factor corresponding to each input signal and node combination;

12.5d) for each node within the neural network layer, summing the products of each input signal and fixed weighting factor combination calculated in the previous step 12.5c);

12.5e) for each node within the neural network layer, calculating a node output by applying an input/output function to the sum calculated in the previous step 12.5d);

12.5f) where the output of each node calculated in step 12.5e) represents the neural network output, displaying at least one node output as an estimated physiological parameter, or 12.5g) where the output of each node calculated in step 12.5e) represents the output of at least one hidden layer node, passing at least one output from outputs calculated in 12.5e) as input to any subsequent layer of nodes in the neural network.

13. A method as defined in claim 12, further comprising the steps of processing the output of the at least one hidden layer node from step 12.5g) by repeating steps 12.5c) through 12.5g) until the at least one node output defined in step 12.5(e)f) representing the estimated physiological parameter has been displayed.

* * * * *